US 8,270,566 B2

(12) United States Patent
McNabb et al.

(10) Patent No.: US 8,270,566 B2
(45) Date of Patent: *Sep. 18, 2012

(54) ADAPTIVE SCANNING IN AN IMAGING SYSTEM

(75) Inventors: Ronald Steven McNabb, Charlestown, MA (US); Nicholas Danvers Penrose Gillett, Redondo Beach, CA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/176,176

(22) Filed: Jul. 5, 2011

(65) Prior Publication Data

US 2011/0261929 A1 Oct. 27, 2011

Related U.S. Application Data

(63) Continuation of application No. 12/437,301, filed on May 7, 2009, now Pat. No. 8,023,619.

(60) Provisional application No. 61/051,410, filed on May 8, 2008.

(51) Int. Cl.
*G01N 23/04* (2006.01)
*H05G 1/30* (2006.01)

(52) U.S. Cl. ............... 378/57; 378/62; 378/86; 378/92; 378/98.7

(58) Field of Classification Search .................... 378/57, 378/62, 86, 92, 98.7
See application file for complete search history.

(56) References Cited

U.S. PATENT DOCUMENTS

| 4,329,654 | A | | 5/1982 | Chamberlain | |
|---|---|---|---|---|---|
| 4,726,046 | A | | 2/1988 | Nunan | |
| 5,040,199 | A | * | 8/1991 | Stein | 378/56 |
| 5,367,552 | A | * | 11/1994 | Peschmann | 378/57 |
| 5,600,700 | A | * | 2/1997 | Krug et al. | 378/57 |
| 5,838,758 | A | * | 11/1998 | Krug et al. | 378/53 |
| 6,430,258 | B1 | | 8/2002 | Spaak | |
| 7,120,226 | B2 | | 10/2006 | Ledoux et al. | |
| 7,492,861 | B2 | | 2/2009 | Chen et al. | |
| 7,580,505 | B2 | | 8/2009 | Kang et al. | |
| 7,664,227 | B2 | | 2/2010 | Speller et al. | |
| 7,742,568 | B2 | | 6/2010 | Smith | |
| 2002/0094059 | A1 | | 7/2002 | Grodzins | |
| 2003/0016790 | A1 | | 1/2003 | Grodzins et al. | |
| 2007/0018117 | A1 | | 1/2007 | Calderon et al. | |
| 2007/0241282 | A1 | | 10/2007 | Clayton et al. | |
| 2008/0211431 | A1 | | 9/2008 | Mishin et al. | |
| 2009/0279664 | A1 | * | 11/2009 | McNabb et al. | 378/62 |
| 2011/0261929 | A1 | * | 10/2011 | Mcnabb et al. | 378/62 |

OTHER PUBLICATIONS

International Search Report and Written Opinion for corresponding International Application No. PCT/US2009/043173, mailed Jul. 6, 2009, 8 pages.

* cited by examiner

*Primary Examiner* — Thomas R Artman
(74) *Attorney, Agent, or Firm* — Fish & Richardson P.C.

(57) ABSTRACT

An object within a region is exposed to a first beam of penetrating radiation. The first beam of penetrating radiation is sensed on a side opposite the region from a source of the first beam. An attenuation of the first beam caused by passing the first beam through the object is determined, the attenuation is compared to a threshold attenuation. If the attenuation exceeds the threshold attenuation, a parameter of a second of beam of penetrating radiation is adjusted based on the determined attenuation.

19 Claims, 5 Drawing Sheets

ADAPTIVE SCANNING IN AN IMAGING SYSTEM

CROSS-REFERENCE TO RELATED APPLICATIONS

This application is a continuation of U.S. patent application Ser. No. 12/437,301, filed May 7, 2009, titled ADAPTIVE SCANNING IN AN IMAGING SYSTEM, which claims the benefit of U.S. Provisional Application No. 61/051,410, filed May 8, 2008, and titled ADAPTIVE SCANNING IN IMAGING SYSTEMS. The contents of these prior applications are incorporated by reference herein in their entirety.

TECHNICAL FIELD

This description relates to adaptive scanning in an imaging system.

BACKGROUND

Cargoes, containers, packages in the transportation system and other objects may be scanned by an x-ray beam in order to produce an image of the object. The image may be analyzed to determine whether the object, or an item within or on the object, includes an item that is hazardous.

SUMMARY

An object is scanned with an adaptive x-ray scanning system that images the object with an x-ray beam and adjust the x-ray beam to account for variations in the density of the object while minimizing the amount of radiation used in the scanning system.

In one general aspect, an imaging system for adaptively scanning a region with a beam of radiation. The imaging system includes a source of radiation configured to produce a beam of penetrating radiation, and to scan an object included in a region. The imaging system also includes a sensor configured to sense radiation passing through the object, and to produce a representation of the sensed radiation. The imaging system also includes a controller coupled to the source of radiation, the controller configured to receive the representation of the sensed radiation, determine an attenuation of the beam caused by the object based on the representation, compare the attenuation to a threshold, and if the attenuation meets the threshold, adjust a parameter of the beam of radiation based on the attenuation.

Implementations may include one or more of the following features. The beam of penetrating radiation may be a pulsed beam of x-ray radiation. The parameter of the beam may be one or more of a collimation of the beam, an intensity of the beam, an energy spectrum of the beam, and a position of the beam. The source of radiation may be configured to direct a first pulse of radiation toward the region, and the controller may be configured to adjust a parameter of the beam of radiation before a second pulse of x-ray radiation is directed toward the region. The system also may include a rotatable filter wheel that is coupled to the controller and positioned between the source and the object. The filter wheel may include a material configured to adjust an intensity or adjust a spectral energy of radiation passing through the material. The rotatable filter wheel may include a first material and a second material, and, to adjust a parameter of the main beam of radiation, the controller may manipulate a timing of a pulse from the source such that the first material is placed in the main beam during a the pulse and the second material is placed in the main beam during a subsequent pulse.

The system also may include a scattered radiation detector coupled to the controller and configured to sense scattered radiation from the region. The controller may be further configured to determine an amount of scattered radiation based on the sensed scattered radiation, compare the amount of scattered radiation to a threshold, and cause the source to reduce an intensity of the beam if the amount exceeds the threshold. The source and the sensor may move relative to the object. The object may move relative to the source or the sensor.

In another general aspect, a method of adaptive scanning includes exposing an object within a region to a first beam of penetrating radiation. The first beam of penetrating radiation is sensed on a side opposite the region from a source of the first beam. An attenuation of the first beam caused by passing the first beam through the object is determined, the attenuation is compared to a threshold attenuation. If the attenuation exceeds the threshold attenuation, a parameter of a second of beam of penetrating radiation is adjusted based on the determined attenuation.

Implementations may include one or more of the following features. The second beam may be the first beam. The first beam may be a pre-scan beam and the second beam may be a main beam separate from the pre-scan beam. The object may be exposed to the pre-scan beam before the object is exposed to the main beam. The pre-scan beam and the main beam may originate from the source of radiation. The first beam may be an x-ray beam and the second beam is an x-ray beam. Adjusting a parameter of the second beam may include adjusting a collimator to adjust a collimation of the second beam. Adjusting a parameter of the second beam may include adjusting a filter positioned between the source of radiation and the object to adjust an intensity or a spectral energy of the second beam. Adjusting a parameter of the second beam may include adjusting a source of the second beam such that an intensity of the second beam is changed. Adjusting a parameter of the second beam may include moving the second beam such that a position of the second beam changes.

In some implementations, the region may be scanned with the adjusted second beam, radiation caused by scanning the region with the adjusted second beam may be sensed, and an image of the region may be generated based on the sensed radiation. The threshold may represent an amount of change in attenuation. The threshold may be an adaptive threshold that varies based on an attenuation caused by portions of the region other than a portion that includes the object. The object may be located at a distance relative to an initial scan location and the threshold may be an adaptive threshold that varies based on the distance.

In another general aspect, an imaging system for adaptively scanning a region with a beam of radiation includes a source system that includes a first source of radiation configured to direct a pre-screen beam toward a region, and a second source of radiation configured to direct a main beam toward the region after the first source directs the pre-screen beam toward the region. The pre-screen beam and the main beam are spatially separated with respect to the region such that the pre-screen beam scans a portion of the region before the main beam scans the portion of the region. The system includes a sensor configured to sense radiation from the pre-screen beam, and produce a representation of the sensed radiation. The system also includes a controller coupled to the source system. The controller is configured to receive the representation of the sensed radiation, determine, from the representation, an amount of attenuation of the pre-screen beam caused by the region, and adjust a parameter of the main beam based on the estimated attenuation prior to directing the main beam toward the region.

Implementations may include one or more of the following features. The pre-screen beam may be a beam of x-ray radiation, and the main beam may be a beam of x-ray radiation having a greater intensity of radiation than the pre-screen beam. The main beam may be a pulsed x-ray beam.

Implementations of any of the techniques described above may include a method, a process, a system, a device, an apparatus, or instructions stored on a computer-readable storage medium. The details of one or more implementations are set forth in the accompanying drawings and the description below. Other features will be apparent from the description and drawings, and from the claims.

DETAILED DESCRIPTION

Figure 1A:
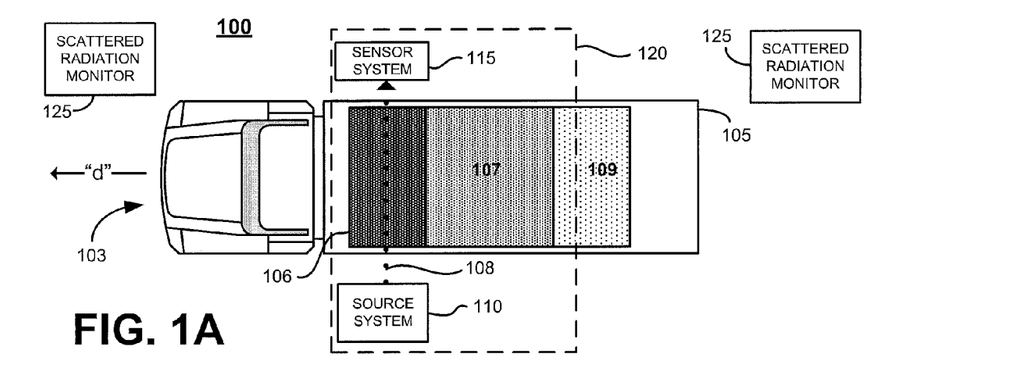
FIGS. 1A-1C illustrate a plan view of an example adaptive scanning system at three different times as an object moves through the system.
Figure 1B:
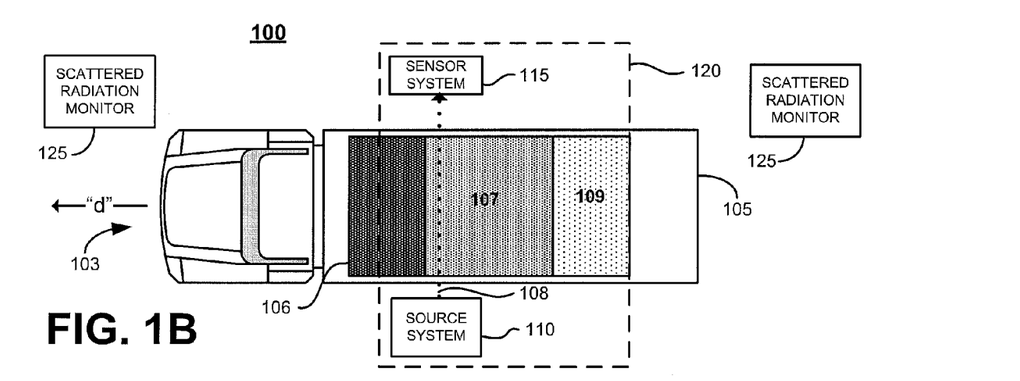
Figure 1C:
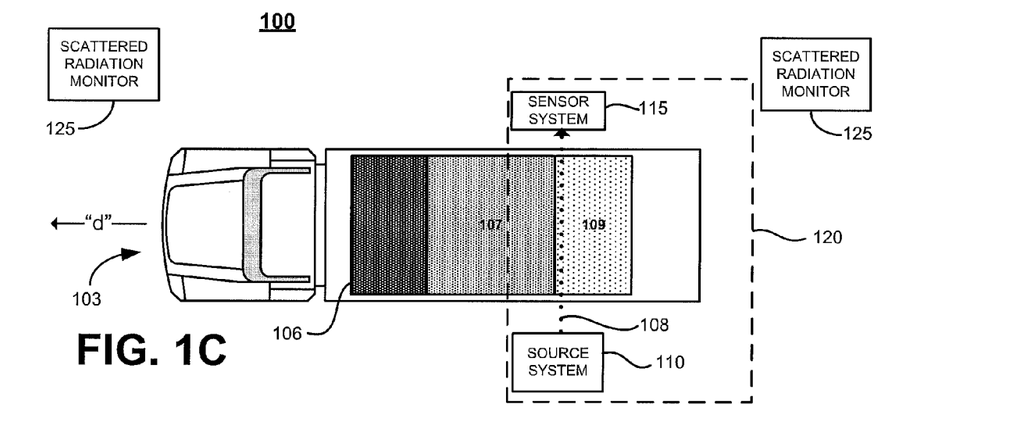

FIGS. 1A-1C illustrate a plan view of an example system 100 for adaptively scanning an object 105 with a single x-ray beam 108 emitted from a source system 100. FIGS. 1A-1C respectively show the system 100 at three different times ($t_1$, $t_2$, and $t_3$) as the x-ray beam 108 scans the object 105 to produce an image of the object 105. In the example shown in FIGS. 1A-1C, the object 105 is a container mounted on the bed of a truck 103.

As discussed in greater detail below, adaptively scanning the object 105 allows a parameter (for example, flux, energy spectrum, position, collimation, pulse rate for pulsed systems, whether to perform material discrimination, and/or scan speed) of the x-ray beam 108 and/or a parameter (for example, integration time, gain, filtering, collimation and/or position) of an imaging sensor system 115 to be adjusted to optimally image objects having unknown and variable densities.

Additionally, adaptive scanning of objects may allow the amount of radiation, or dose rate, outside of an exclusion zone 120 to remain below an acceptable safety level or allow the size of the exclusion zone 120 to be reduced. The exclusion zone 120 is a region in the vicinity of the source system 110 and the scanned object 105 that is closed to personnel for safety reasons. The techniques discussed below may be used in systems that image objects with x-ray beams of continuous radiation (which are used in many baggage screening systems) and those that image objects with pulsed x-ray beams. Pulsed x-ray beams are used in many systems that use relatively high energy x-ray radiation, such as systems used to screen cargoes or other large objects.

X-ray systems may have a fixed level of flux (e.g., x-ray beam intensity) and filtering that is determined by competing objectives. To obtain high penetration into an imaged space and concomitant high image quality, the beam flux (or intensity) may be increased and the filtering of the beam may be reduced to allow as much radiation as possible to reach the imaged space. In contrast, for safety, the dose rate (e.g., an amount of radiation a person or object is exposed to over a period of time) to the object scanned and to personnel in the vicinity of the system 100 is set below the local radiation safety limits and as low as reasonably achievable. The desire for a low dose rate may require that the beam intensity be kept relatively low. The adaptive scanning imaging system 100 (or "adaptive system" 100) balances these competing objectives to ensure safety while also producing a high-quality image of the object 105.

In the example of FIGS. 1A-1C, the object 105 is a container 105 that is mounted on the bed of a truck 103. The system 100 is a drive-through portal scanning system, and the truck 103 passes through the portal 100 in a direction "d." In other examples, the object 105 may be, for example, a cargo (a shipping container, or a vehicle) or an item (such as a trunk, a suitcase, a purse, or a briefcase) transported by a traveler. The container 105 has a high-density region 106 (which may be a material such as lead), a mid-density region 107 (which may be a material such as concrete, stone, and/or plastic), and a low-density region 109 (which may be an empty portion of the container 105).

The object 105 is imaged using the x-ray beam 108. The x-ray beam 108 is emitted from a source system 110 and enters the container 105. If the x-ray beam 108 is penetrating enough relative to the container 105 and materials within the container 105, a portion of the x-ray beam passes through the container 105 and is sensed by the imaging sensor system 115. Additionally, radiation scattered from the container 105 is sensed by one or more scattered radiation monitors 125 that are out of the beam path of the x-ray beam 108. The scattered radiation monitors 125 may be inside of the exclusion zone 120 or outside of the exclusion zone 120. In some implementations, scattered radiation monitors are located inside of the exclusion zone 120 and outside of the exclusion zone 120.

The scattered radiation monitors 125 measure an amount of scattered x-ray radiation and may be used to ensure that the amount of radiation outside of the exclusion zone 120 remains within a defined dose rate. Thus, the monitors 125 are used to ensure that the amount of radiation leaving the exclusion zone 120 is at or less than a safe amount. As discussed above, the scattered radiation monitors 125 may be inside of the exclusion zone 120. Placing the scattered radiation monitors 125 inside of the exclusion zone 120 results in the monitors being closer to the beam 108. As a result, scattered radiation monitors inside of the exclusion zone 120 tend to receive more radiation than scattered radiation monitors that are outside of the exclusion zone 120, thus making measurements of the dose rate easier.

However, because the amount of radiation outside of the exclusion zone 120 is of interest, an amount of radiation sensed by a scattered radiation monitor that is inside of the exclusion zone 120 is extrapolated or otherwise converted to an amount of scattered radiation (or radiation dose) outside of the exclusion zone 120. Additionally, a scattered radiation monitor that is placed inside the exclusion zone 120 may be more easily mounted in a stable position as compared to a scattered radiation monitor that is located outside of the exclusion zone 120. For example, the system 100 may be mounted on a mobile platform that is mounted on a truck and the scattered radiation monitors may be fixedly mounted on the truck.

Radiation sensed by the imaging sensor system 115 and/or the scattered radiation monitors 125 is used to adjust a parameter of the x-ray beam 108 and/or the imaging sensor system 115 such that the object 105 is adaptively scanned. The system 100 adapts to the characteristics of the container 105 and/or the environment within the exclusion zone 106 to adaptively scan the container 105. The system 100 may adapt by, for example, adjusting a parameter of the x-ray beam 108, by adjusting the imaging sensor system 115, or by adjusting a parameter of both the imaging sensor system 115 and the x-ray beam 108.

In the example shown in FIGS. 1A-1C, the system 100 is a drive-through portal through which a truck 103 is driven. Because the driver remains in the truck 103 as the contents of the container 105 are scanned, the amount of radiation to which the driver is exposed must be minimized. However, the container 105 may contain dense materials, thus requiring that the x-ray beam 108 be relatively intense. Accordingly, a trade-off exists between improving the penetration of the x-ray beam 108 into the container 105 by exposing the container to a more intense x-ray beam such that a high-quality image is produced and ensuring that the driver of the truck 103, the contents of the truck, and the region around the system 100 are not exposed to an unsafe level of radiation while the truck 103 passes through the drive-through portal 100.

Referring to FIG. 1A, at a time time=$t_1$, the source system 110 exposes the high-density portion 106 of the container 105 to the x-ray beam 108. The sensor system 115 senses x-ray radiation passing through the container 105 and produces data representing the amount of sensed radiation such that an image of the container 105 may be generated. The high-density portion 106 causes a relatively large amount of attenuation of the x-ray beam 108, thus the imaging sensor 115 senses a relatively small amount of radiation. In response, the source system 110 may increase the intensity of the beam 108 such that more x-ray radiation passes through the high-density portion 106. Concurrently, the scattered radiation monitors 125 sense an amount of radiation that is scattered from the container 105 or other objects in the vicinity of the container 105, to ensure that the increase in the intensity of the x-ray beam 108 does not cause the amount of radiation outside of the exclusion zone 120 to exceed a defined safe dosage rate.

Referring to FIG. 1B, at a later time, time=$t_2$, the x-ray beam 108 scans the mid-density portion 107 of the container 105. When the contents of the container 105 transition from the high-density portion 106 to the mid-density portion 107, the sensing system 115 senses an increased amount of radiation because more of the x-ray beam 108 penetrates through the container 105 due to the lower density of materials in the path of the x-ray beam 108. Accordingly, the x-ray beam 108 may be adapted to, for example, reduce the intensity of the x-ray beam 108 to a level that produces an acceptable image of the mid-density portion 107 but has a lower intensity than the x-ray beam 108 that imaged the high-density region 106. Reducing the intensity of the beam in this manner may allow a reduction in the total amount of x-ray radiation to which the driver is exposed while still producing a high-quality image of the mid-density portion 107.

Referring to FIG. 1C, at a later time, time=$t_3$, the x-ray beam 108 has progressed to the low-density portion 109 of the container 105. Similar to the situation discussed with respect to FIG. 1B, the intensity of the x-ray beam 108 may be reduced shortly after the transition into the low-density region 109.

As a result of adapting a parameter (which is the intensity in the example of FIGS. 1A-1C) of the x-ray beam 108 to account for the variation in density of the materials in the container 105, the container 105 is scanned with an x-ray beam 108 having a flux sufficient to image the various regions of the container 105 while also minimizing the driver's exposure to x-ray radiation. Thus, the total amount of radiation that the driver of the truck is exposed to may be reduced as compared to a system that exposes the entire container 105 to a x-ray beam having an intensity sufficient to adequately image the high-density portion 106. The quality of the image of the container 105 produced by the imaging sensor system 115 may be improved as compared to a system that imaged the entire container 105 with an x-ray beam having sufficient intensity to image the low-density portion 100 or the mid-density portion 107 but not the high-density portion 106. Additionally, because the system 100 is able to account for and adjust to the changes in the density of the material within the container 105, the image of the container 105 may be improved as compared to a system that assumes that the density of scanned objects remains relatively constant or within a pre-defined range.

Figure 2:
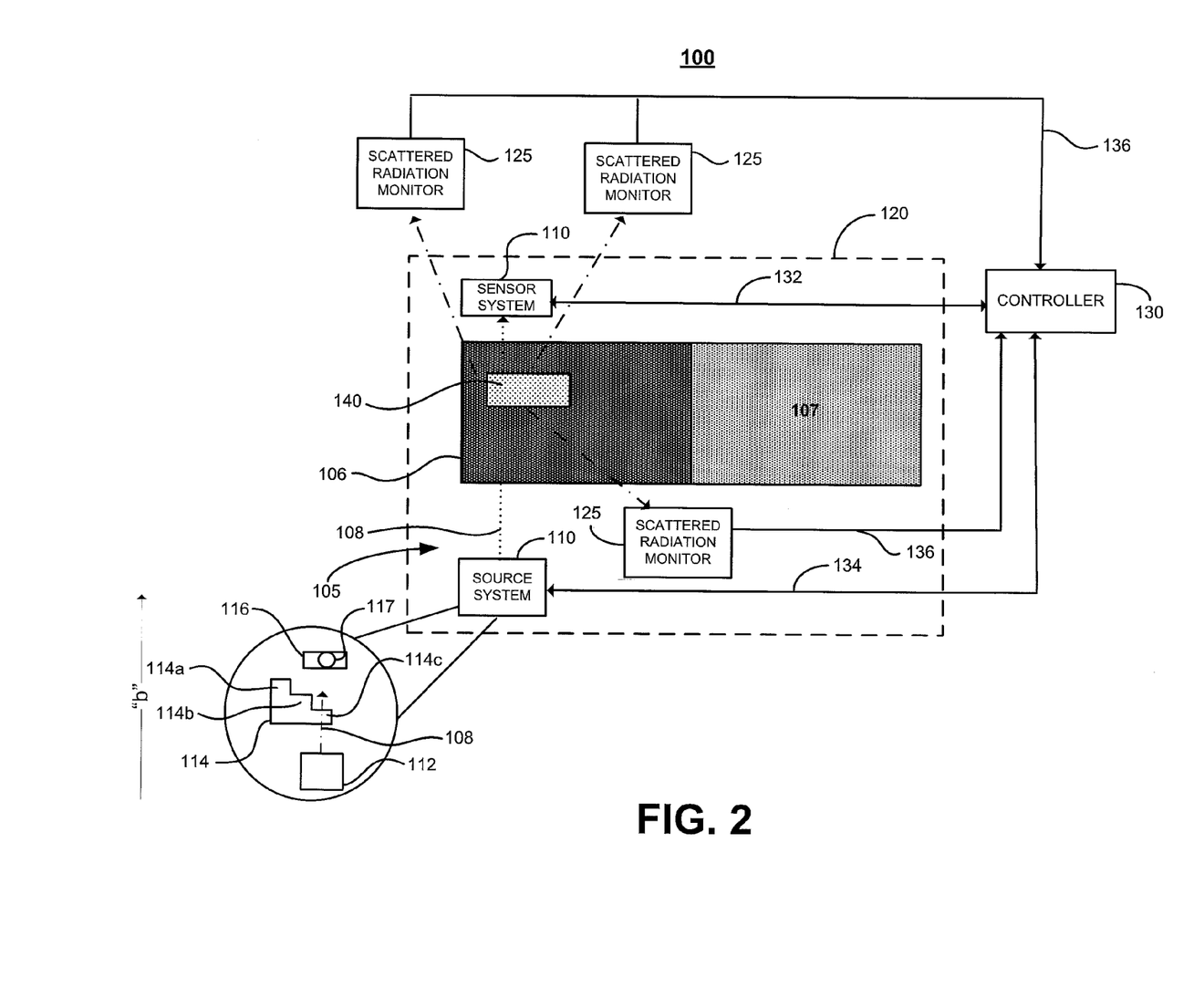
FIG. 2 illustrates another plan view of the adaptive scanning system shown in FIG. 1.

FIG. 2 shows another plan view that illustrates the system 100 at the time $t_1$ in greater detail. The source system 110 exposes the high-density region 106 to the x-ray beam 108. The x-ray beam 108 enters the container 105, interacts with the materials in the container 105 and is attenuated by an amount that depends on the density of the materials, emerges from the container 105, and is sensed by the imaging sensor system 115. X-ray radiation that emanates beyond the exclusion zone 120 is detected by one or more scattered radiation monitors 125. The scattered radiation monitors 125 may be placed on any or all sides of the exclusion zone 120.

As discussed above with respect to FIGS. 1A-1C, the container 105 is adaptively scanned by adjusting a parameter of the x-ray beam 108, the source system 110, and/or the imaging sensor system 115. The parameters may be adjusted by a controller 130 that is configured to receive data from the imaging sensor system 115, the source system 110, and the scattered radiation monitors 125 and to produce a control signal that the controller 130 provides to the source system 110 and/or the sensor system 115. The control signal causes a corresponding adjustment in a parameter of the source system 110 or the imaging sensor 115. The controller 130 receives data from and provides control signals to the imaging sensor 115 through a control line 132. The controller 130 receives data from and provides control signals to the source system 110 through a control line 134. The controller receives data from the scattered radiation monitors 125 through a control line 136. The control lines 132, 134, and 136 may be wired or wireless data connections.

The source system 110 includes a source 112 that generates the x-ray beam 108 and a filter 114 that may be placed in the path of the beam 108. In the example shown in FIG. 2, the thickness of the filter 114 along the direction "b" of the propagation of the x-ray beam 108 varies. In particular, the filter 114 has a thick portion 114a, a mid portion 114b, and a thin portion 114c. Each of the portions 114a, 114b, and 114c is wider than the physical beam width of the x-ray beam 108 in a direction that is perpendicular to the direction "b." For example, the portions 114a, 114b, and 114c may each be five centimeters in the direction "b." The beam 108 becomes attenuated by passing through the filter 114, with the amount of attenuation being proportional to the amount of material through which the beam passes. Thus, by positioning a particular one of the portions 114a, 114b, and 114c in the path of the beam 108, the intensity of the x-ray radiation reaching the container 105 may be controlled.

For example, as shown in FIG. 2, the dense region 106 includes a low-density material 140. Thus, when the x-ray beam 108 scans the portion of the dense region 106 that includes the low-density material 140, the x-ray beam 108 is attenuated less than the beam is attenuated by the dense region 106 that do not include the low-density material 140. As a result, when scanning the portion of the region 106 that includes the low-density material 140, the imaging sensor system 115 detects an increase in flux as compared to the portion of the dense region that precedes the low-density material 140. The sensor system 115 may send a representation of the amount of flux detected to the controller 130, and the controller 130 produces a control signal indicating that the intensity of the beam 108 may be reduced. The controller 130 provides the control signal to the source system 110. The source system 110 may respond by moving the filter 114 such that the portion 114a or 114b is in the path of the beam 108 rather than the portion 114c. In some implementations, the source system 110 may reduce the intensity of the x-ray beam 108 in another manner, such as reducing the current to the source 112 such that less x-ray radiation is produced, resulting in an x-ray beam of lower intensity. In some implementations in which the beam 108 is a pulsed beam, the dose rate may be altered by changing the pulse rate of the beam 108. For example, initially the system may integrate two pulses per vertical line, but switching the system to a single pulse per sample while also halving the pulse rate reduces the dose rate by half.

Other parameters of the x-ray beam 108 may be adjusted as a result of the data provided by the imaging sensor system 115. For example, the change in flux received as a result of encountering the low-density material 140 or by transitioning from the high-density portion 106 to the mid-density portion 107 may be an indication that these regions of the container 105 include materials of interest such that a more detailed image of these portions of the container would be useful. A more detailed image of the portion may be generated by exposing the region to the x-ray beam 108 for a longer time by reducing the scan speed. The controller 130 may provide a control signal to the source system 110 to reduce the speed at which the source system 110 sweeps the beam 108 along the container 105.

In addition to the intensity and scan speed, other parameters of the source system 110 may be adjusted to adaptively scan the container 105. For example, the source system 110 also includes a collimator 116 having an adjustable opening 117 through which the x-ray beam 108 passes. To make the x-ray beam 108 more collimated, the size of the opening 117 is reduced, and, to make the x-ray beam 108 less collimated (e.g., a larger beam), the size of the opening 117 is increased. A more collimated beam may be used to produce more refined data of a particular region of interest within the container 105. Additionally, a more collimated beam may result in less scatter of x-ray radiation outside of the exclusion zone 120. Thus, the collimation of the beam 108 may be adjusted based on the amount of scattered radiation detected by the scattered radiation monitors 125.

In another example, the energy spectrum of the beam 108 may be adjusted by passing the beam 108 through a filter such as the filter 114. The filter 114 adjusts an energy spectrum and an intensity of radiation passing though the filter 114. In implementations in which the source system 110 produces a pulsed beam, the filter may be a rotatable filter wheel that includes multiple materials, each of which modify the energy spectrum of the beam 108 in a different manner. The angular position of the filter wheel may be used to determine the timing of a pulse from the source such that the pulsed x-ray beam is filtered by a particular material that is positioned in the path of the beam at the time that the pulse is emitted from the source 110.

Additionally, the position of the beam 108 relative to the container 105 may be adapted by moving the source system 110 relative to the container 105. For example, the object scanned by the drive-through portal immediately prior to scanning the truck 103 may be a passenger vehicle suspected of having weaponizable materials in a rear trunk region of the vehicle. Thus, the source system 110 may be placed relatively close to the ground when the truck 103 enters the drive-through portal. The imaging sensor system 110 may sense a high amount of x-ray radiation as a result of the x-ray beam 108 not striking the container 105. As a result, the controller 130 may send a signal to the source system 110 to cause the source system 110 to move higher until the imaging sensor system 115 senses a decrease in flux caused by the presence of the container 105.

Instead of, or in addition to, adapting a parameter of the x-ray beam 108 to account for the situation encountered during a scan, the imaging sensor system 115 also may be adjusted. For example, the gain of the detectors included in the imaging sensor system 115, the filtering and collimation of the radiation that reaches the detectors, and the positioning of the detectors may be adjusted. The gain of the detectors may be increased when the imaging sensor system 115 senses a relatively small about of radiation. Increasing the gain of the detectors may allow detection of a relatively weak x-ray signal from the container 105 that may be the result of the x-ray beam 108 passing through very dense material. Increasing the gain of the detectors may allow the dense region to be imaged without resorting to increasing the intensity of the x-ray beam 108 or by increasing the intensity of the x-ray beam 108 by an amount less than would otherwise be required. As a result, the radiation dosage to the personnel and objects in the vicinity of the system 100 may be decreased while still producing a high-quality image of the container 105. The vicinity of the system 100 includes areas within the exclusion zone 120 and outside of the exclusion zone 120. Similarly, the filtering of the beam emerging from the container 105 may be reduced to allow as much radiation as possible to reach the imaging sensor system 115 without having to increase the intensity of the x-ray beam 108.

Additionally, whether or not to perform material discrimination at all may be determined from the data received from the imaging sensor system 115. Material discrimination tends to be less effective for highly attenuating cargo. In this case, the energy spectrum of the beam 108 may be altered such that the object is scanned at a single (or nearly single energy), which may result in improved penetration of the object by the beam 108. In some implementations in which the source system 110 produces a separate high-energy x-ray beam and a low-energy x-ray beam, one of the beams may be switched off when it is determined that material discrimination is not desired. Accordingly, the source system 110 and/or the imaging sensor system 115 may be adjusted to optimize the performance of the system 100 based on data from the source system 110, the imaging sensor system 115, and/or the scattered radiation monitors 125. By adjusting the parameters of these components as discussed above, the penetration of the x-ray beam 108 may be increased, the resolution of the images produced by the imaging sensor system 115 may be increased, the materials discrimination may be improved, the radiation dosage around the system 100 is decreased, and the throughput of the system may be increased.

Figure 3:
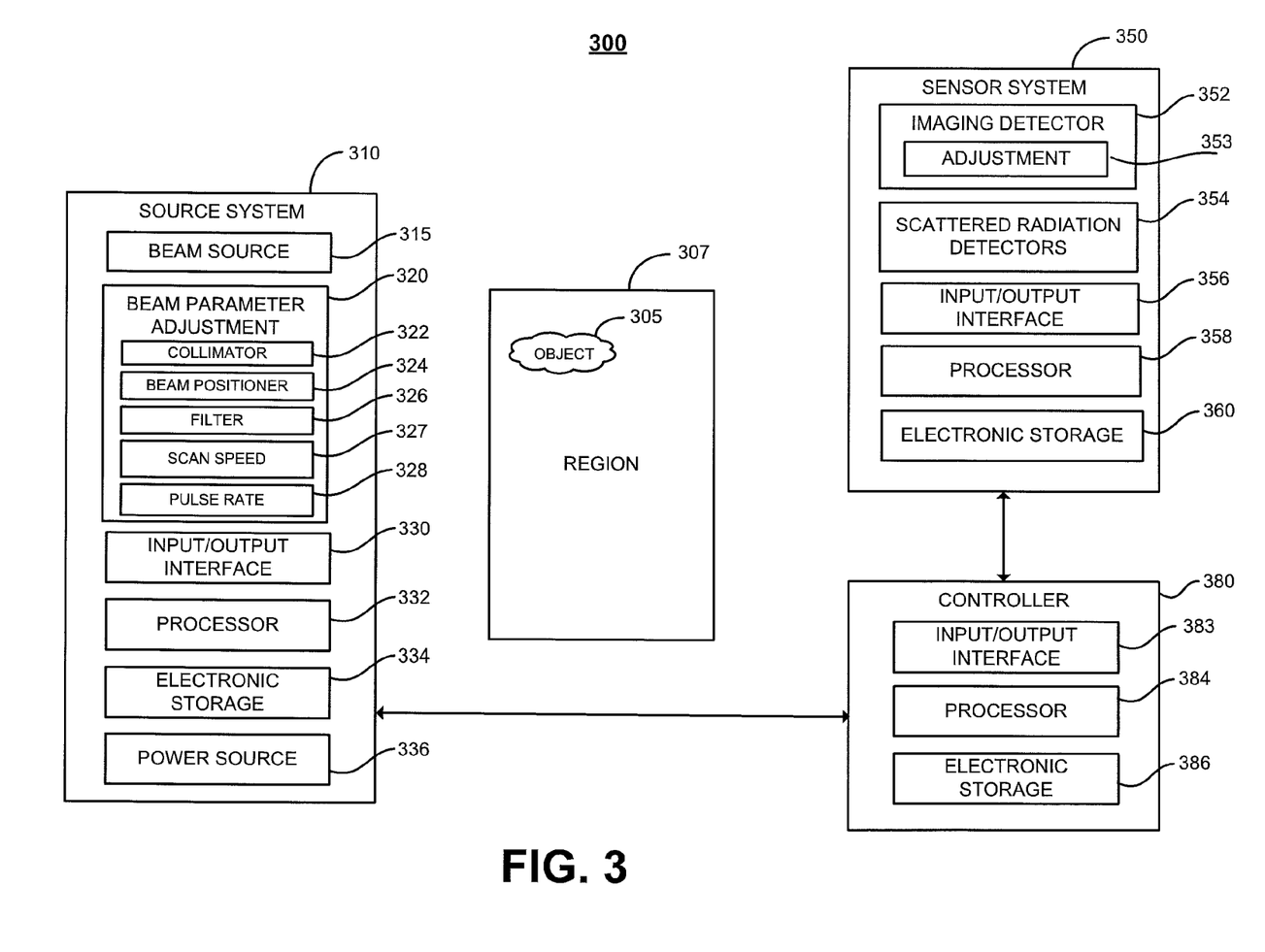
FIG. 3 illustrates a block diagram of an example system for adaptively scanning an object.

FIG. 3 shows a block diagram of an example system 300 for adaptively scanning an object 305 that is within a region 307. The region 307 may be a passageway or opening that holds or conveys luggage in a baggage screening system, and the object 305 may be one of several pieces of luggage in the baggage screening system at a given time. In other examples, the region 307 may be a container mounted on the bed of a truck (such as the container 105 that is mounted on the truck 103 discussed above with respect to FIGS. 1A-1C) that passes through a fixed drive-through portal system. The system 300 adaptively scans the object 305 to produce a high-quality image of the object 305 and other portions of the region 307, while also minimizing the amount of x-ray radiation to which personnel in the vicinity of the system 300 are exposed.

The system 300 includes a source system 310, a sensor system 350, and a controller 380. The source system 310 produces an x-ray beam that scans the object 305 and the region 307. X-ray radiation that passes through the region 307 and the object 305 is sensed by the sensor system 350. The controller 380 is configured to be in communication with the sensor system 350 and the source system, and the controller 380 produces a control signal that is configured to cause an adjustment of a parameter of the x-ray beam, the source system 310, and/or the sensor system 350 based on data received by the controller.

In a system in which the beam source 315 produces a pulsed beam (e.g., the system 300 is a pulsed system), the adjustment of the parameter may occur within one or two pulses of receiving the data from the sensor system 350 that indicates that an adjustment would be beneficial. In a system in which the beam source 315 produces a continuous beam (e.g., the system 300 is a continuous or non-pulsed system), the adjustment of the parameter may occur within a pre-set time following the receipt of data from the sensor system 350 indicating that an adjustment would be beneficial. The pre-set time is such that an image of the region 307 is not noticeably degraded due to frequent adjustment.

The source system includes a beam source 315, a beam parameter adjustment 320, an input/output module 330, a processor 332, an electronic storage 334, and a power source 336. The beam source 315 produces an x-ray beam that has an energy spectrum (e.g., a band or range of photons having a particular energy) and a peak or maximum energy. The x-ray beam enters the region 307 and is attenuated by the materials in the region 307. The x-ray beam is used to image the region 307, and a parameter of the x-ray beam (such as the intensity, the energy spectrum, the position, or the collimation) may be adjusted to account for variations in density of the material in the region 307 or to maintain x-ray radiation outside of an exclusion zone in the vicinity of the system 300 within acceptable limits. The beam source 315 may produce a beam that has a constant energy (e.g., a continuous beam) or a pulsed beam. In the case of a pulse beam, the width (or duration) of the pulse may be adjusted as may the frequency of the pulses.

The x-ray beam produced by the beam source 315 may have a maximum energy of 1-12 mega-electron volts (MeV) in the case in which the system 300 is used to image dense objects such as large cargoes that include dense and/or thick materials. In these examples, the bean source 315 may be a linac. In other examples, the system 300 may be used to image checked baggage. In these examples, the beam source 315 may have a maximum energy between about 100 keV and 10 MeV. In some implementations, the beam source 315 is a source of neutral particles (such as neutrons). In these implementations, the beam source 315 may be a particle accelerator. In some implementations, the source system 310 may include multiple types of sources, each of which produce different particles, and the source system 310 may be configured to allow selection between the different types of sources.

The source system 310 also includes the beam parameter adjustment 320. The beam parameter adjustment 320 adjusts one or more parameters of the beam produced by the beam source 315 in response to receiving a control signal from the controller 380. The beam parameter adjustment 320 includes a collimator 322, a beam positioner 324, a filter 326, a scan speed adjustment 327, and a pulse rate adjustment 328. The x-ray beam is collimated by passing through an opening in the collimator 322 that has an adjustable size. The collimator 322 may be made from a dense material, such as lead, that is impenetrable to x-ray radiation. The size of the opening in the collimator 322 may be adjusted with a motor that is coupled to the collimator 322 and configured to cause the opening to change size. The nominal size of the opening of the collimator 322 may be, for example, three millimeters.

The beam parameter adjustment 320 also includes the beam positioner 324, which positions the beam that is emitted from the beam source 315. The beam positioner 324 may position the beam by, for example, moving the beam source 315 or by directing the beam emitted from the beam source 315 in a particular direction.

The beam parameter adjustment 320 also includes the filter 326. The filter 326 is a material that changes the energy spectrum and intensity of a beam of radiation passing through the filter. The filter 326 may be made from, for example, plastic or aluminum. The amount of filtering of the beam performed by the filter 326 depends on the material of the filter and the amount of material through which the beam passes. The filter 326 may be made of a single material of varying thickness, such as the filter 114 discussed above with respect to FIG. 2. In these implementations, the intensity and/or energy spectrum of the beam may be adjusted differently depending on which portion of the filter the beam passes through. In some implementations, the filter 326 includes multiple filtering materials, each of which has different filtering properties. In these implementations, the filter 326 may have a variable thickness along the direction of beam propagation (such as the filter 114), or the filter 326 may have a uniform thickness.

In implementations in which the beam source 315 produces a pulsed beam, the filter 326 may be a continuously rotating wheel that includes filtering materials. The rotating wheel is positioned such that only one of the materials is in the path of the beam from the beam source 315 at any given time. The filter wheel also may include blank regions in which no filtering material is located such that the filter wheel does not filter the beam when the blank is in the bath of the beam. In implementations that use the filter wheel, the filtering of the beam may be adjusted between pulses by controlling the timing of the beam source 315 based on an angular position of the filter wheel. In particular, the timing of the pulse is such that a pulse is emitted from the beam source 315 when a particular material is in the beam of the pulse. Thus, in pulsed systems the filtering of the beam from the beam source 315 may potentially be more finely controlled, and controlled on a pulse-by-pulse basis, with the filter wheel as compared using a filter such as the filter 114.

The beam parameter adjustment 320 also includes the scan speed adjustment 327 and the pulse speed adjustment 328. The scan speed adjustment 327 allows the speed of the scanning of the object 305 and the region 307 to be increased or decreased. For example, in implementations in which the beam source 315 moves with respect to the object, the scan speed adjustment 327 may increase or decrease the speed at which the beam source 315 moves in order to, respectively, increase or decrease the scan speed. In implementations in which the beam source 315 produces a pulsed beam, the pulse speed adjustment 328 allows the frequency of the pulses and/or the duration of the pulses to be adjusted.

The source system 310 also includes the input/output interface 330, the processor 332, the electronic storage 334, and the power source 336. The input/output interface 330 allows the source system 310 to communicate with components outside of the source system 310, such as the controller 380 and the sensor system 380. Additionally, the input/output interface 330 allows the source system 310 to accept data and commands through an interface device such as a mouse or keyboard and to present data through an interface device such as a visual display. The input/output interface 330 may accept commands from a human operator of the system 300 or from an automated process. The electronic storage 334 stores instructions that, when executed, cause the processor 332 to perform operations such as changing the current to the beam source 315 such that the intensity of the beam produced by the beam source 315 is correspondingly changed. The power source 336 provides power to the source system 310 and may be, for example, a customized or off-the-shelf power supply that provides sufficient power to allow the beam source 315 to produce an x-ray beam and to power the other components of the sensor system 310.

The system 300 also includes the sensor system 350, which senses radiation that passes through or is scattered from the region 307 and the object 305 as a result of exposure to the beam produced by the beam source 315. The sensor system 350 includes an imaging detector 352, a scattered radiation detector 354, and input/output interface 356, a processor 358, an electronic storage 360, and a power source 362. Although, in the example shown in FIG. 3, the imaging detector 352 and the scattered radiation detector 354 are both included in the sensor system 350, these components are not necessarily placed in the same physical location or housed within a single housing. In particular, the imaging detector 352 is located in the path of the beam produced by the beam source 315 and the scattered radiation detector 354 is placed out of the path of the beam. The imaging detector 352 senses radiation in order to produce an image of the object 305, and the scattered radiation detectors 354 sense radiation that is scattered out of the beam path (and thus poses a potential threat to personnel in the vicinity of the system 300). The imaging detector 352 may be located in the imaging sensor system 115 discussed above with respect to FIGS. 1A-1C and 2, and the scattered radiation detectors 354 may be placed throughout an area in the vicinity of the system 300 (such as in an arrangement similar to the ones shown in FIGS. 1A-1C and 2).

The imaging detector 352 is a detector that is in the beam path of the beam source 315 and senses radiation that passes through the object 305 in order to produce an image of the object 305. The imaging detector 352 produces a representation of the amount of radiation sensed from the region 307 and provides this representation to the controller 380 and/or the source system 310. Additionally, the imaging detector has an adjuster 353 that allows adjustment of the integration time of the imaging detector 352. Increasing the integration time may allow the imaging detector 352 to sense more radiation without increasing the intensity of the beam from the beam source 315. The representation may be a value that expresses the intensity of the radiation or the amount of flux sensed by the imaging detector 353. The imaging detector 353 may be an array of imaging detectors that are arranged in a vertical line or two-dimensional array with respect to the region 307. The imaging detector 352 is aligned with the beam source 315. In implementations in which the beam scans the region 307 by moving with respect to the region 307, the imaging detector 352 and the beam source 315 are coupled such that the beam source 315 and the imaging detector 352 move along the region 307 together.

The imaging detectors 352 sense radiation from the portion of the region 307 that is currently irradiated with the beam from the beam source 315, and the representation of the amount of sensed radiation is stored in the electronic storage 360. Once the imaging detector 352 has received radiation from the entire region 307, an image of the region 307 and the object 305 may be generated based on the representations of the amount of sensed radiation.

The imaging detectors 352 may be a scintillator crystal that produces visible light in response to being struck by x-ray radiation. The imaging detector 352 may be made from any scintillator material such as, for example, cadmium tungstate ($CdWO_4$ or CWO), thallium-activated cesium iodide CsI(TI), cadmium zinc telluride (CdZnTe), or rare-earth phosphors. The intensity of the visible light is proportional the number of photons striking the scintillator. The visible light produced by the scintillator may be sensed by an optical detector, such as a photodiode or a photomultiplier tube, that is coupled to the scintillator and produces an electrical signal having a current proportional to the amount of visible light sensed by the optical detector. The electrical signal is digitized by an analog-to-digital converter (A/D) to produce a digital signal having a discrete value. The digital signal may be considered to be a representation of an amount of radiation sensed by the imaging detector 352, and the representation indicates how much attenuation is caused by the portion of the region 307 that is currently imaged. The amount of attenuation that a material causes an incident x-ray beam to undergo is an indication of the density of a material.

The scattered radiation detector 354 monitors radiation that is scattered out of the beam path from the region 307 and/or the object 305. The scattered radiation detector 354 is used to ensure that the amount of radiation outside the exclusion zone does not exceed a safety limit. The exclusion zone is a region in the vicinity of the system 300 in which personnel do not enter due to the exclusion zone having dose rates above applicable safety standards. Thus, placing the scattered radiation detectors outside of the exclusion zone allows the detectors to be used to measure radiation in a region that should not have an amount of radiation that is unsafe for personnel. In some implementations, scattered radiation detectors are placed inside of the exclusion zone. In these implementations, radiation received by the scattered radiation detectors inside the exclusion zone may be extrapolated to determine a dose rate outside of the exclusion zone. The amount (or dosage) of radiation is measured over a period of time, and the maximum dosage may be provided as an amount of radiation received over an hour. If the amount of radiation measured by the scattered radiation detector exceeds the maximum allowable amount, the source system 310 may, for example, reduce the intensity of the beam produced by the beam source 315 in order to reduce the amount of radiation that is scattered out of the exclusion zone.

The scattered radiation detector 354 has a larger active area than the imaging detector 352, and, thus, the scattered radiation detectors are relatively low-resolution detectors that are generally not used for imaging. The scattered radiation detector 354 may have an active area that ranges between, for example, a few square centimeters ($cm^2$) to over a square meter ($m^2$) in size. The scattered radiation detector 354 may be an ionization detector that has a relatively slow response time.

The scattered radiation detector 354 senses the amount of radiation and stores a representation of the amount of energy in the electronic storage 360 and/or provides the representation to the controller 380. Monitoring the representation over a period of time allows the dosage rate over the period of time to be determined. When the dosage exceeds a recommended dosage, the controller 380 may provide a signal to the source system 310 such that the intensity of the beam produced by the beam source 315 is reduced.

The system 300 may use the dose measured by the scattered radiation detectors 354 over a time period ranging from a few milliseconds (which may be the duration of a single pulse in a pulsed system) to adjust the beam quickly or the system 300 may integrate the dose measured over a longer time period and adjust the beam only after it becomes more clear that the dose rate is too high (exceeds a safety limit). The system 300 may track the total dose rate over many scans to limit the dose rate within, for example, an hour or day.

The scattered radiation detectors 354 may detect a short burst of radiation when an object first enters the beam because, when the object is not in the beam, the scatter from the object is not shielded by the object. This initial burst may last about a fraction of a second. Because this initial short burst is an anomaly that typically occurs only as the object enters the beam, lower the dose rate based on the short burst of radiation because the measured dose may decrease within a fraction of a second as the object moves into the beam and through the system 300. Accordingly, how far into the scan the object has traveled (or how long the object has traveled in the scan) may be considered when deciding whether to limit the dose rate by reducing the intensity of the beam produced by the beam source 315.

The scattered radiation detectors 354 are used to keep dose rates outside of the exclusion zone within safety limits. The scattered radiation detectors 354 may be placed inside and/or outside of the exclusion zone. When placed inside of the exclusion zone, calculations are applied to the dose rate measured at the location of the scattered radiation detector inside of the exclusion zone to extrapolate to the dose rate at another location, such as a location outside of the exclusion zone. As compared to placing a scattered radiation detector outside of the exclusions zone, placing the scattered radiation detector inside of the exclusion zone allows the scattered radiation monitor to receive a larger dose rate because the dose rate is higher inside of the exclusion zone. As a result, the scattered radiation detector receives a higher amount of radiation in the same amount of time, which makes it possible to measure the dose rate more quickly. Additionally, scattered radiation detectors placed inside of the exclusion zone may also be more easily mounted in a stable position compared to scattered radiation detectors that are positioned outside of the exclusion zone. For example, a scattered radiation detector positioned inside of the exclusion zone may be mounted on a fixed structure that is part of the system 300. Such a structure may or may not be available outside of the exclusion zone.

The system 300 also includes the controller 380. The controller 380 receives data from and provides control signals to the source system 310 and the sensor system 350. The controller 380 includes an input/output interface 383 that allows the controller 380 to exchange data and commands with the source system 310 and the sensor system 350. The controller also includes an electronic storage 386 that stores data that the controller 380 uses to produce control signals that cause the source system 310 and the sensor system 350 to adjust a parameter to adapt the system 300 to the environment. The electronic storage may store representations of the amount of attenuation caused by the region 305 from the imaging detector 352. In addition to storing the representation of the amount of intensity currently sensed by the imaging detector 352, the electronic storage 386 also may store representations of the amount of intensity sensed by the imaging detector 352 and/or the scattered radiation detector 354 in previous scans of different objects. This data represents the amount of attenuation caused by other objects and the resulting adjustments to beam and sensor parameters. This data may be used to determine initial parameters of the beam produced by the source 315 before the beam scans the region 307. Additionally, the historical data may be used to filter the data received from the sensor system 350 (perhaps by averaging the current data with the historical data) to smooth out sharp transitions in attenuation such that the beam parameters are only adjusted when relatively large changes density occur in the imaged object (which are reflected as relatively large changes in measured attenuation).

The electronic storage 386 also stores instructions that, when executed, cause the processor 384 to access data from the electronic storage 386 to produce control signals that cause the sensor system 380 and/or the source system 310 to adjust a parameter of the beam or the imaging detector 352.

Although in the example shown in FIG. 3, the controller 380 is a separate component of the system 300 that is in communication with the source system 310 and the sensor system 380, that is not necessarily the case. In some implementations, the controller 380 is part of the source system 310 and/or the sensor system 380 and the source system and the sensor system are communicatively coupled directly to each other.

Figure 4:
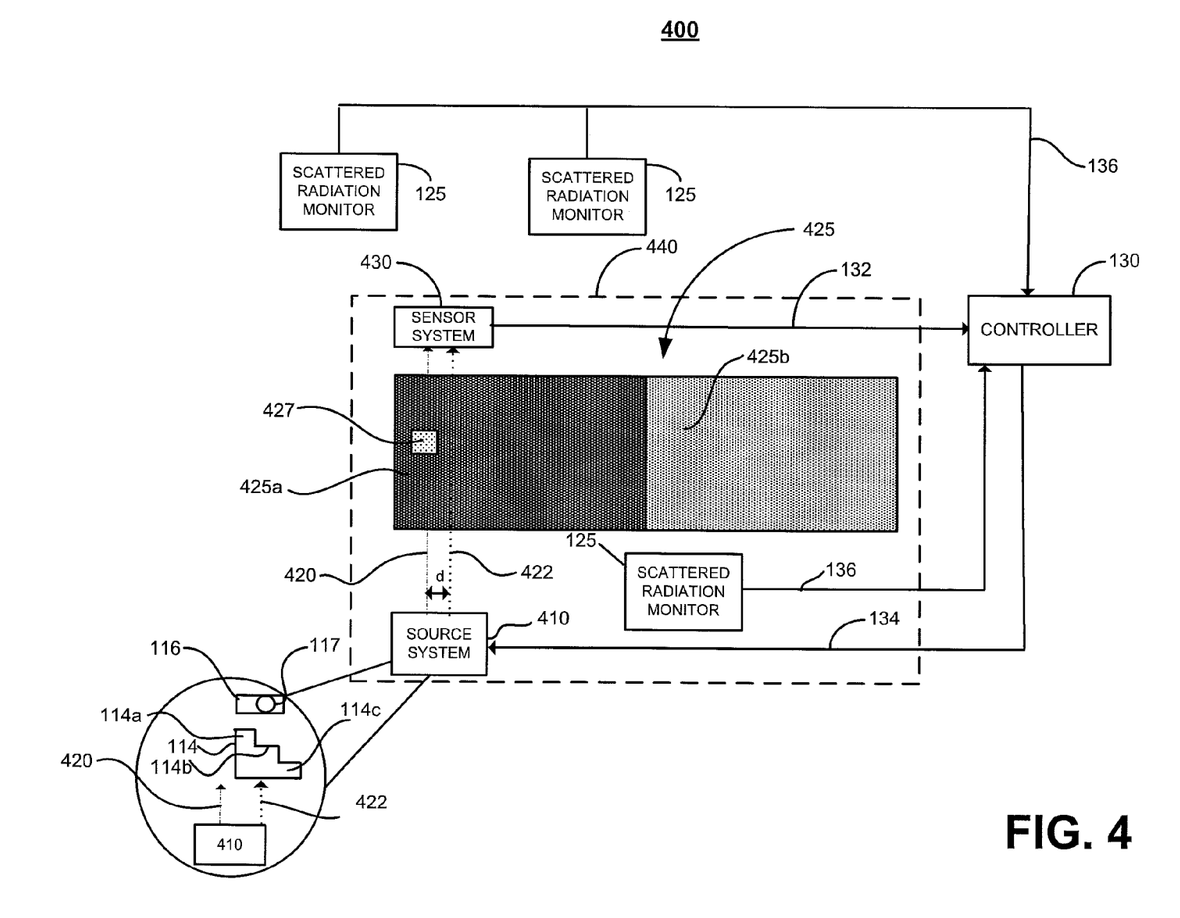
FIG. 4 illustrates a plan view of an example two-beam adaptive scanning system.

FIG. 4 shows a plan view of an example system 400 for adaptively scanning an object. The system 400 is similar to the system 100 discussed above with respect to FIGS. 1A-1C and FIG. 2, except the system 400 includes a source system 410 that produces two beams, a pre-scan beam 420 and a main (imaging) beam 422, rather than with a single imaging beam. The pre-scan beam 420 and the main beam 422 are separated in a direction "d" along an imaged region 425 such that the pre-scan beam 420 irradiates a particular portion 427 of the region 425 before the main beam 422 irradiates the portion 427 of the region 425. The imaged region includes a high-density portion 425a and a lower-density portion 425b. The separation between the pre-scan beam 420 and the main beam 422 along the direction "d" may be, for example, a few centimeters to over a meter. The separation between the pre-scan beam 420 and the main beam 422 may be selected based on the scan speed and the frequency of the expected variations in the region 425.

Both the pre-scan beam 420 and the main beam 422 are detected by imaging detectors in a sensor system 430. The pre-scan beam 420 and the main beam 422 may both be x-ray beams, and the pre-scan beam 420 and the main beam 422 may be either continuous or pulsed x-ray beams. The source system 410 may include one source that produces both the pre-scan beam 420 and the main beam 422 or the source system 410 may include two sources, one that produces the pre-scan beam 420 and one that produces the main beam 422.

The amount of attenuation of the pre-scan beam 420 caused by the portion 427 is used to set a parameter of the main beam 422 before the main beam 422 images the portion 427. Thus, using the pre-scan beam 420 may allow the system 400 to adapt to objects having unknown densities such that the lowest intensity beam that still creates a high-quality image of the objects may be used to image the objects.

In particular, the system 400 scans the portion 427 of the region 425 with the pre-screen beam 420 before the main beam 422 scans the portion 427 such that the beam parameters of the main beam 422 may be set before the main beam 422 scans the region 425. For example, a low density object may be scanned with a low level of flux and/or high filtration in order to reduce the dose rate (e.g., the amount of radiation to which personnel outside the exclusion zone 440 are exposed). In contrast, higher-density objects may be scanned with the highest flux possible and little or no filtering in order to provide the best penetration through the high-density object possible. The beam parameters may be adjusted as the region 425 passes through the system 400 to provide an optimal imaging/dose rate balance for each portion of the region 425. The dose rate may be only as high as necessary to scan a given region 425. In addition, higher density objects provide greater shielding against scattered x-rays so the dose rates at points outside the system for a higher dose rate operating mode may not be much greater than for a low dose rate mode.

A sensor system 430 having an imaging detector is positioned behind the region 425 and in the beam path of the source system 410. Data from the sensor system 430 is used to determine what beam and detector settings provide optimum imaging properties for the main beam 422. Based on the data from the sensor system 430, the parameters of the main beam 422 (e.g., energy, flux, filtering, and collimation) and the detectors 430 (e.g., gain, position, and collimation) are adjusted as the region 425 passes through the system (or as the source system 410 and the sensor system 430 pass by the region 425). The use of a pre-scan beam 420 to help determine and/or set parameters of a main (or, more generally, another) beam 422 of radiation and/or detectors may be referred to as adaptive scanning. Allowing the system 400 to vary the characteristics of the main beam 422 and detectors 430 based on the situation, context, or environment may be referred to as adaptive scanning. Adaptive scanning may result in, for example, higher penetration depths and improved imaging properties, while also minimizing the average radiation dose to both the objects scanned and to personnel around the system.

In some implementations, the integrated intensity of the pre-scan beam 420 may be reduced to further limit the amount of radiation to which personnel around the system 400 are potentially exposed. Approaches to reducing the integrated intensity include more tightly collimating or highly filtering the pre-scan beam 420, splitting the pre-scan beam 420 into a set of thin pencil beams, emitting the pre-scan beam 420 for only a fraction of the time such that parts of the region 425 being scanned are sampled as the pre-scan beam 420 travels through the system 400 and, when the pre-scan beam 420 originates from a different source than the main beam 422, the pre-scan beam 420 may be of lower energy and/or intensity than the main beam 422. Splitting the pre-scan beam 420 into thin pencil beams allows the region 425 being sampled by the pre-scan beam 420 to be sampled at multiple points (rather than pre-scanning every position).

The pre-scan beam 420 also may serve a secondary purpose. For instance, the pre-scan beam 420 may provide a second view of the region 425 at a different angle or scan at a different energy for materials discrimination purposes.

Figure 5:
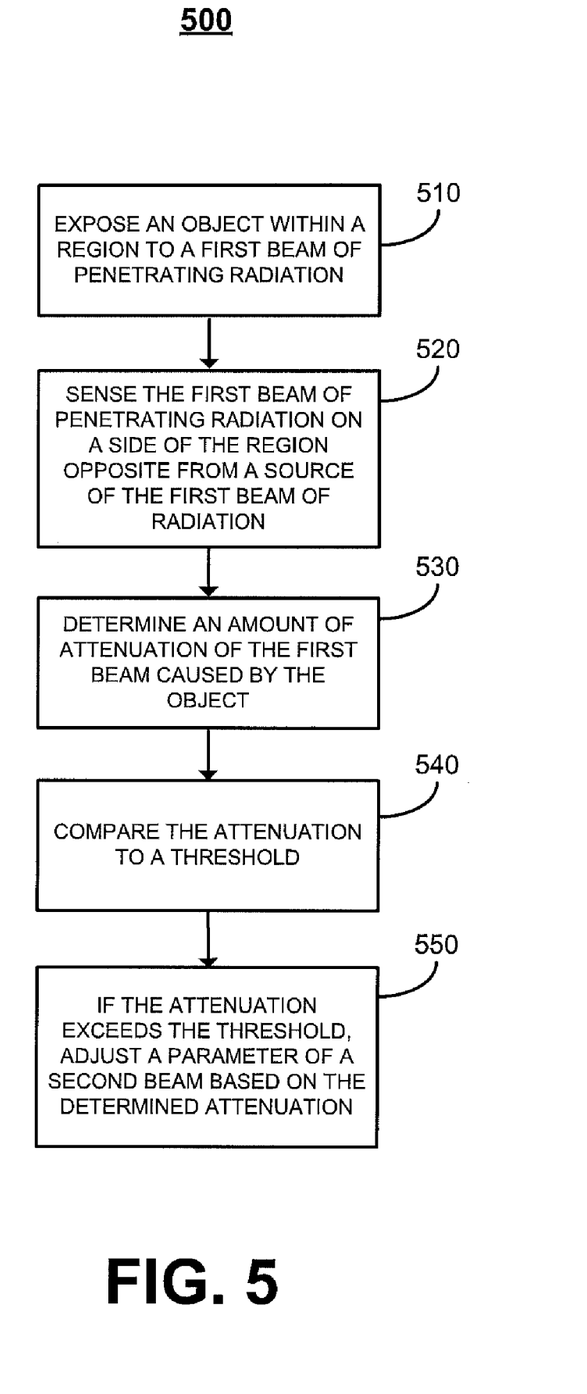
FIG. 5 illustrates an example process for adaptively scanning an object.

FIG. 5 shows an example process 500 for adaptively scanning an object with an x-ray beam. The process 500 may be performed by a single-beam adaptive scanning system such as the system 100. Alternatively, the process 500 may be performed by an adaptive scanning system that includes both a pre-scan beam and an imaging beam, such as the system 400 discussed with respect to FIG. 4. The process 500 may be performed by one or more processors included in such an adaptive scanning system. For example, the process 400 may be performed by the controller 380 and the processor 384 discussed above with respect to FIG. 3.

An object within a region is exposed to a first beam of penetrating radiation (510). The first beam of penetrating radiation may be an x-ray beam from a source such as the beam source 315, or the first beam of penetrating radiation may be another beam of radiation that is energetic enough to penetrate the object 305. In some implementations, the first beam of penetrating radiation is a pre-scan beam of radiation, such as the pre-scan beam 420 discussed above with respect to FIG. 4, that spatially precedes an imaging beam of radiation. The first beam of penetrating radiation is sensed on a side of the region that is opposite from the source of radiation (520). The first beam of radiation may be sensed by an imaging detector such as the imaging detector 352.

An amount of attenuation of the first beam of radiation that is caused by the object is determined (530). The amount of attenuation of the first beam of radiation caused by the object is an indication of the density of the object. The amount of attenuation of the first beam of radiation may be compared to a previous amount of attenuation of the first beam of radiation to determine a percent change in the amount of attenuation. The previous amount of attenuation may be an amount of attenuation that was recently determined for an adjacent portion of the scanned object or for an amount of attenuation for a portion of the region that is not adjacent to the object. In some implementations, the previous amount of attenuation may be an amount of attenuation that occurred in an earlier scan of a different object. A significant change in the amount of attenuation triggers an adjustment in a parameter of the beam or the sensing system.

The amount of attenuation is compared to a threshold (540). The amount of attenuation may be a percent change in attenuation, and the threshold may be a percent change in attenuation above which a parameter of the beam or the detector is adjusted. The threshold may be a threshold that is predefined and stored in the system, or the threshold may be an adaptive threshold that changes based on the characteristics of the imaged region. For example, if the imaged region has many relatively minor transitions between dense regions and non-dense regions that occur within a small space (such as a solid material that has large pockets of air formed within it), the threshold may be set high such that the parameters are only changed when a significant change occurs. Adjusting the parameters of the beam or detector too often may result in a blocky image, or an image with other undesirable artifacts.

In some implementations, the threshold may be adapted based on a distance that the object is located relative to an initial scan point. The initial scan point may be the first location at which objects enter the system to be scanned. For example, referring to FIGS. 1A-1C, the initial scan point may be the left-most portion of the region 106. In this example, the threshold attenuation may be lower as compared to positions closer to the initial scan point. This is because as the object moves further away from the initial scan point, there may be more shielding and distance between the object and the beam. For example, the driver of the truck 103 is further from the beam 108 when the truck 103 is at the position shown in FIG. 1C as compared to the position of the truck in FIG. 1A. Thus, the threshold at the position of FIG. 1C may be relatively lower, which results in the beam being adjusted (for example, by increasing the intensity of the beam 108) more frequently. For example, when the beam 108 is positioned as shown in FIG. 1C, the beam intensity may be increased without as much risk to the driver of the truck 103 as compared to increasing the beam intensity when the beam 108 is positioned as shown in FIG. 1A. Instead of a distance, a time since the start of the scan may be used in determining the threshold.

If the attenuation exceeds the threshold, a parameter of a second beam is adjusted based on the determined attenuation (550). In some implementations, the second beam is the same beam as the first beam. These implementations are single-beam systems such as the system 100 discussed above with respect to FIGS. 1A-1C and FIG. 2. In other implementations, the second beam is a beam that is separate from the first beam. For example, the second beam may be the main beam 422 and the first beam may be the scan beam 420 discussed with respect to FIG. 4. In either implementation, the parameters of the second beam that may be adjusted include the intensity of the beam, the collimation of the beam, the position of the beam, and the energy spectrum of the beam. More than one parameter of the second beam may be adjusted. Additionally, a parameter of the imaging detector, such as the gain, filtering or collimation of the beam received by the detector, or the position of the detector also may be adjusted. In implementations in which the second beam is a pulsed beam, adjusting a parameter of the second beam may include adjusting the timing of the pulse of the second beam such that the pulse passes through a particular material included in a rotating filter wheel.

A number of implementations have been described. Nevertheless, it will be understood that various modifications may be made without departing from the scope of the disclosure.

What is claimed is:

1. An imaging system for adaptively scanning a region with a beam of radiation, the imaging system comprising:
    a source system comprising:
        a first source of radiation configured to direct a pre-screen beam toward a region, and
        a second source of radiation configured to direct a main beam toward the region after the first source directs the pre-screen beam toward the region, the pre-screen beam and the main beam being spatially separated with respect to the region such that the pre-screen beam scans a portion of the region before the main beam scans the portion of the region;
    a sensor configured to:
        sense radiation from the pre-screen beam, and
        produce a representation of the sensed radiation;
    a controller coupled to the source system and configured to:
        receive the representation of the sensed radiation,
        determine, from the representation, an amount of attenuation of the pre-screen beam caused by the region,
        adjust a parameter of the main beam based on the determined attenuation prior to directing the main beam toward the region;
        receive a representation of the sensed scattered radiation,
        determine an amount of scattered radiation based on the representation,
        compare the amount of scattered radiation to a threshold, and
        if the amount of scattered radiation meets or exceeds the threshold, reduce an intensity of one or more of the pre-screen beam or the main beam.

2. The system of claim 1, wherein the pre-screen beam is a beam of x-ray radiation, and the main beam is a beam of x-ray radiation having a greater intensity of radiation than the pre-screen beam.

3. The system of claim 1, wherein the main beam is a pulsed x-ray beam.

4. The system of claim 3, further comprising a filter wheel coupled to the controller and positioned between the second source and the object, the filter wheel including a material configured to adjust an intensity or adjust a spectral energy of radiation passing through the material.

5. The system of claim 1, wherein the pre-screen beam scans the region at a different angle than the main beam.

6. The system of claim 1, wherein the pre-screen beam comprises penetrating radiation of a first energy, and the main beam comprises penetrating radiation of a second energy, the first energy and the second energy being different.

7. The system of claim 1, further comprising a scattered radiation monitor coupled to the controller, the scattered radiation monitor being configured to sense radiation scattered from the region.

8. The system of claim 1, wherein the controller being configured to adjust a parameter of the main beam based on the determined attenuation comprises the controller causing an intensity of the main beam to increase or decrease.

9. The system of claim 1, wherein the controller being configured to adjust a parameter of the main beam based on the determined attenuation comprises the controller causing a change in a spectral energy of the main beam.

10. The system of claim 1, further comprising a filter positioned in a path of the main beam, the filter configured to adjust an intensity or spectral energy of a portion of the main beam that passes through the filter.

11. The system of claim 10, wherein the filter comprises a thickness that varies in a direction of propagation of the main beam.

12. A method of adaptive scanning, the method comprising:
    directing a pre-screen beam of penetrating radiation towards a region, the pre-screen beam being directed from a first source of radiation;
    determining an amount of attenuation of the pre-screen beam;
    adjusting a parameter of a main beam of penetrating radiation based on the amount of attenuation of the pre-screen beam;
    directing the adjusted main beam of penetrating radiation towards the region, the main beam being directed from a second source of radiation that is spatially separated from the first source of radiation such that the pre-screen beam scans the region before the main beam scans the region;
    receiving a representation of an amount of scattered radiation;
    determining an amount of scattered radiation;
    comparing the amount of scattered radiation to a threshold; and
    if the amount of scattered radiation meets or exceeds the threshold, adjusting a parameter of the main beam of penetrating radiation based on the amount of attenuation of the pre-screen beam comprises adjusting an intensity of the main beam such that the amount of scattered radiation is below the threshold.

13. The method of claim 12, wherein the pre-screen beam is an x-ray beam, and the main beam is an x-ray beam, the main beam having a greater intensity than the pre-screen beam.

14. The method of claim 13, wherein one or more of the pre-screen beam or the main beam are pulsed beams.

15. The method of claim 12, wherein adjusting a parameter of the main beam comprises adjusting a source of the main beam such that an intensity of the main beam is changed.

16. The method of claim 12, further comprising:
    receiving a representation of the adjusted main beam as attenuated by passing through the region; and
    generating an image of the region based on the received representation.

17. The method of claim 12, wherein adjusting a parameter of a main beam of penetrating radiation based on the amount of attenuation of the pre-screen beam comprises directing the main beam through a filter positioned between a source of the main beam and the region, the filter being configured to adjust an intensity or spectral energy of the main beam.

18. The method of claim 12, wherein directing the adjusted main beam towards the region comprises directing the main beam of radiation towards the region at a different angle than directing the pre-screen beam of radiation.

19. A method comprising:
   directing a pre-screen beam of penetrating radiation towards a region;
   determining an amount of attenuation of the pre-screen beam;
   adjusting a parameter of a main beam of penetrating radiation based on the amount of attenuation of the pre-screen beam;
   directing the adjusted main beam of penetrating radiation towards the region, the pre-screen beam and the main beam being spatially separated such that the pre-screen beam scans the region before the main beam scans the region;
   receiving a representation of an amount of scattered radiation;
   determining an amount of scattered radiation;
   comparing the amount of scattered radiation to a threshold, and
   if the amount of scattered radiation meets or exceeds the threshold, adjusting a parameter of the main beam of penetrating radiation based on the amount of attenuation of the pre-screen beam comprises adjusting an intensity of the main beam such that the amount of scattered radiation is below the threshold.

\* \* \* \* \*